United States Patent [19]

Blum et al.

[11] Patent Number: 4,608,368

[45] Date of Patent: Aug. 26, 1986

[54] 1-HYDROXY-1,1-DIPHOSPHONIC ACIDS AND CYTOSTATIC USE THEREOF

[75] Inventors: Helmut Blum, Duesseldorf; Wolfgang Greb, Duesseldorf-Kaiserswerth; Hinrich Moeller, Monheim; Dietrich Schmaehl, Heidelberg; Harald Schnegelberger, Leichlingen; Hannsjoerg Sinn, Wiesloch; Franz Wingen, Heidelberg, all of Fed. Rep. of Germany

[73] Assignee: Henkel Kommanditgesellschaft auf Aktien, Duesseldorf, Fed. Rep. of Germany

[21] Appl. No.: 753,479

[22] Filed: Jul. 10, 1985

[30] Foreign Application Priority Data

Jul. 13, 1984 [DE] Fed. Rep. of Germany ....... 3425812

[51] Int. Cl.$^4$ .................... C07F 9/38; A61K 31/135; A61K 31/085; A61K 31/10
[52] U.S. Cl. .............................. 514/107; 260/502.5 C
[58] Field of Search .................. 260/502.5 C; 514/107

[56] References Cited

U.S. PATENT DOCUMENTS

| | | | |
|---|---|---|---|
| 3,202,579 | 8/1965 | Berth et al. | 260/502.5 C |
| 3,617,342 | 11/1971 | Kandler et al. | 260/502.5 C |
| 3,617,576 | 11/1971 | Korst | 260/502.5 C |
| 3,668,138 | 6/1972 | Hoover et al. | 260/502.5 C |
| 3,816,518 | 6/1974 | Kerst | 260/502.5 C |
| 4,098,814 | 7/1978 | Sommer et al. | 260/502.5 C |
| 4,230,700 | 10/1980 | Francis | 514/107 |
| 4,371,527 | 2/1983 | Bentzen et al. | 514/107 |
| 4,416,877 | 11/1983 | Bentzen et al. | 514/107 |
| 4,503,049 | 3/1985 | Biere et al. | 514/107 |

FOREIGN PATENT DOCUMENTS

| | | |
|---|---|---|
| 307135 | 5/1973 | Austria . |
| 2130794 | 11/1973 | Fed. Rep. of Germany . |
| 2405254 | 8/1975 | Fed. Rep. of Germany . |
| 2658961 | 6/1978 | Fed. Rep. of Germany . |
| 2702631 | 7/1978 | Fed. Rep. of Germany . |
| 2943498 | 5/1981 | Fed. Rep. of Germany . |
| 3151038 | 7/1983 | Fed. Rep. of Germany . |
| 2113688 | 8/1983 | United Kingdom ........... 514/107 |

OTHER PUBLICATIONS

Arch. Pharm. (Weinheim) 311, 184–195 (1978).

*Primary Examiner*—J. E. Evans
*Attorney, Agent, or Firm*—Ernest G. Szoke; Henry E. Millson, Jr.; Mark A. Greenfield

[57] ABSTRACT

1-hydroxy-1,1-diphosphonic acid compounds corresponding to the following general formula $$\text{Cl-CHR-CH}_2 \diagdown \text{N} \diagup \text{Cl-CHR}_1\text{-CH}_2 \diagup \bigg\langle \text{ring with X} \bigg\rangle \text{-Y}_n\text{-Z}_m\text{-}\underset{\underset{\text{PO}_3\text{H}_2}{|}}{\overset{\overset{\text{PO}_3\text{H}_2}{|}}{\text{C}}}\text{-OH} \quad (I)$$

in which
R and $R_1$ represent hydrogen or methyl,
X represents hydrogen, halogen, amino, which may be acyl substituted, lower alkyl, which may be substituted by amino or acyl substituted amino, or lower alkoxy,
Y represents O, S or NH
Z represents lower alkylene, which may be substituted by amino or acyl substituted amino, and
m and n have the value 0 or 1 with the proviso that, where n is 1, m is also 1;
and to pharmacologically compatible salts thereof.

The invention also relates to a process for producing these compounds and to their use in pharmacological preparations having cytostatic activity.

11 Claims, No Drawings

1-HYDROXY-1,1-DIPHOSPHONIC ACIDS AND CYTOSTATIC USE THEREOF

BACKGROUND OF THE INVENTION

1. Field of the Invention

The present invention relates to novel 1-hydroxy-1,1-diphosphonic acid compounds, processes for their preparation, pharmaceutical compositions containing them, and methods for their use as cytostats.

2. Description of Related Art

Hitherto known cytostatic agents for the treatment of bone tumors are non-tumor-specific and, hence, generally require very high dosages with corresponding toxic side effects, cf. H. Breidthaupt, E. Kuenzlen, (1983), "High dose methotrexate for osteosarcoma: toxicity and clinical results", Oncology 40, 85–89.

Efforts have also been made chemically to modify cytostatically active compounds in such a way that, after administration, they accumulate at the tumor sites. The concept of this research trend is based on the known fact that selected compounds belonging to certain structure types tend to accumulate in certain organs of the living organism, so that by combining an organ-specific component such as this with a cytostatically active component it would be possible to promote the transport of the cytostatically active component into the target organ. However, these efforts have not yet proved successful, at least in the majority of cases. In general, the chemically modified compounds are no longer organ-specific. This applies, for example, to the attempt to couple steroid hormones (particularly oestradiol and testosterone) with alkylating groups in order thus to attack tumors in tissues in which these hormones normally accumulate, cf. for example Journal of Medicinal Chemistry, 1979, Vol. 22, No. 2, 200-202.

In an attempt to treat liver tumors with alkylating derivatives of sulfonamides, of which the parent compound accumulates in the liver, organ specificity was thereby lost. It was only in exceptional cases which could not be predicted with any certainty that the research concept mentioned above could be put into practice more or less effectively, cf. for example Arch. Pharm. (Weinheim) 311, 184–195 (1978).

The use of nitrogen mustard derivatives is known and is standard practice for the treatment of various neoplasms. Chlorambucil, which is the approved name for 4-(4-bis-(2-chloroethyl)-amino)-phenylbutyric acid, is a substance which has been therapeutically used for some years, although it is non-specific to bone tumors. Many structurally analogous compounds have been proposed for the same purpose.

Finally, it is also known that certain polyfunctional diphosphonic acids, particularly alkane diphosphonic acids, containing a 1-hydroxy-1,1-diphosponic acid group, have the property of being absorbed by apatite and accumulate in the skeleton, cf. for example Austrian patent application 307 135 and German application 24 05 254.

DESCRIPTION OF THE INVENTION

An object of the present invention is to improve the prospects of chemotherapy in the treatment of bone tumors. More particularly, an object of the present invention is to provide a cytostatic agent which combines demonstrable accumulation in the bones or in bone tumors with significant cytostatic activity.

The present invention is based on the discovery that, by combining the two above-mentioned action mechanisms in one compound—apatite affinity through the diphosphonic acid group and cytostatic activity through an alkalating nitrogen mustard group—improved results can be obtained on the tumor. Accordingly, the invention provides a cytostatic agent for the treatment of bone tumors which represents a considerable improvement over hitherto known therapeutic agents.

In a first embodiment, therefore, the present invention relates to new chemical compounds which combine the above-mentioned action principles of organ specificity and cytostatic activity. In another embodiment, the invention relates to a process for producing these new compounds. Finally, the invention relates to the use of these compounds for the treatment of bone tumors and to pharmaceutical preparations containing the new compounds for such use.

The new cytostatically active, organ-specific compounds are new 1-hydroxy-1,1-diphosphonic acid compounds corresponding to the following formula

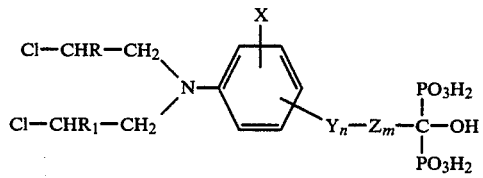

and pharmacologically compatible acid or base addition salts thereof. In general formula I, R and $R_1$ can be the same or different, and represents hydrogen or methyl, X represents hydrogen, halogen, an amino group or substituted amino group, a lower alkyl radical optionally substituted by an amino or substituted amino group, or a lower alkoxy radical, Y represents one of the radicals O, S or NH, Z represents a staight-chain or branched chain alkylene radical which may optionally be substituted by an amino group or substituted amino group. The symbols m and n are the numbers 0 or 1, with the proviso that, where n is 1, m is also 1.

That part of the molecule which is attached to the aromatic ring through Y will frequently be present in the p-position to the mustard group, although it may also be present as a substituent in the m- or o- position. In one group of preferred compounds, both R and $R_1$ are hydrogen. It is also preferred for X to represent hydrogen. When X represents halogen, preferred halogen substituents are fluorine, chlorine or bromine. Preferred lower alkyl radicals or lower alkoxy radicals for X contain no more than 5 carbon atoms and, more preferably, no more than 3 carbon atoms. Characteristic examples are the methyl or ethyl radical and the corresponding methoxy or ethoxy radicals. The substituent X may contain an amino group in the case of amino-substituted alkyl radicals, or X may itself be an amino group. In this connection, the amino groups in X and Z above can optionally be substituted, for example by a lower acyl radical

where $R_2$ is a $C_1$–$C_6$ alkyl group) e.g. by an acetyl radical. The straight-chain or branched chain and optionally substituted alkylene radical Z preferably contains a total of no more than 10 and preferably no more than 5 carbon atoms. In this connection, it is also preferred that no more than 5 carbon atoms and, in particular, no more than 3 carbon atoms are present in the straight part of the chain. The following are preferred radicals for Z:
—CH$_2$—, —(CH$_2$)$_2$—, —(CH$_2$)$_3$—, —CHCH$_3$—CH$_2$—,

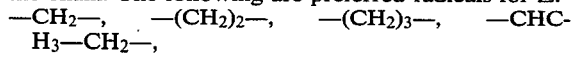

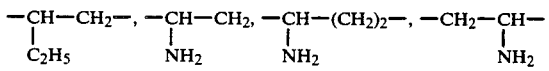

As already mentioned, m and n may have the values 0 or 1, but with the proviso that, where n is 1, i.e. where one of the radicals O, S or NH is actually present, m is also 1.

In one group of preferred compounds of general formula I, n has the value 0, so that the radical Y drops out. Instead, the alkylene radical Z is directly atached to the aromatic ring. For such compounds m can also have the value 0, but is preferably 1.

One particularly important new compound corresponding to the above general formula is 4-(4-(bis(2-chloroethyl)-amino)-phenyl)-1-hydroxy-butane-1,1-diphosphonic acid, which has the structural formula

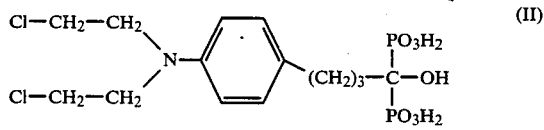

The free acids corresponding to compounds of general formula I and, in particular, to that of formula II fall within the scope of the invention. However, these acids are particularly suitable for pharmacological application in the form of their pharmacologically compatible acid addition salts with the nitrogen atom, or base addition salts with one or both phosphonic acid groups. Examples of base addittion salts such as these are alkali metal, alkaline earth metal and/or ammonium salts, such as sodium, potassium, magnesium, ammonium and substituted ammonium salts. Both partial salts, in which only some of the acid protons are replaced by other cations, and also full salts fall within the scope of the invention. As stated above, acid addition salts with acids that are pharmacologically compatible in the form of their salts are also within the scope of the present invention and are in fact more stable than the base addition salts. Suitable acids include hydrogen halides, e.g. HCl, HBr, and HI; sulfuric acid; and phosphoric acid. Salts which show a substantially neutral reaction (pH approx. 5–9) can be of advantage. Mixtures of different salts and also mixtures of the free acids with salts also fall within the scope of the invention. The free acids themselves presumably form a partial inner salt with their tertiary nitrogen atom on the nitrogen mustard group.

The new compounds corresponding to general formula I and, in particular, to that of formula II and its salts are both cytostatically active and also accumulate in bone tumors. These compounds show only very slight mutagenic potential in the so-called Ames test. It is known that other alkylating agents used in the chemotherapy of cancer are strong mutagens. Since mutagens are themselves suspected of causing cancer, the virtual absence of mutagenic activity is another significant advantage of the new compounds. Irrespective of their cytostatic activity, the new compounds also show some antimicrobial activity, e.g. against gram-positive bacteria, i.e., cocci, such as Staph. aureus and Strept. mutans, with an inhibiting concentration of 1000 ppm.

The starting material used for the production of the compound of formula II is chlorambucil, i.e., 4-(4-bis-(2-chloroethyl)-amino)- phenyl butyric acid. The terminal carboxyl group of chlorambucil is converted into the corresponding 1-hydroxy-1,1-diphosphonic acid group using a known reaction mechanism. This aspect of the invention produces 1-hydroxyalkane-1,1-diphosphonic acids by reacting the corresponding aliphatic carboxylic acids substituted or unsubstituted in the alkane residue with H$_3$PO$_3$ and a dehydrating agent such as a phophorus-halogen compound, resulting in conversion of the terminal carboxyl group into the 1-hydroxy-1,1-diphosphonic acid group. Reaction conditions that be employed herein can be found in for example, German patent Nos. 2,130,794, 2,658,961 and 2,943,498 and German application Nos. 27 02 631 and 31 51 038 which describe related reactions with other starting materials.

It is known from those publications that substituted and/or unsubstituted alkane carboxylic acids can be reacted with H$_3$PO$_3$ and phosphorus-halogen compounds, particularly coresponding chlorine derivatives of phosphorus, to form the corresponding 1-hydroxy-1,1-diphosphonic acid components. Suitable phosphorus-halogen compounds are, in particular, PCl$_3$, POCl$_3$ and/or PCl$_5$. In this connection, it is also possible to use anhydrous phosphoric acid, so-called "crystallized phosphoric acid", cf. German application No. 31 51 038.

Conversion of the carboxyl group into the diphosphonic acid group takes place by a complex reaction mechanism. The phosphorus-halogen compound acts primarily as a dehydrating agent, although the hydrolysis product of the phosphorus-halogen component which accumulates may also participate in the substitution reaction. If phosphorus-halogen components of pentavalent phosphorus are used exclusively, the H$_3$PO$_3$ is used in at least the stoichiometrically necessary quantity—2 moles of H$_3$PO$_3$ per mole of chlorambucil—in one preferred embodiment of the process of the invention. However, if the phosphorus-halogen compound is at least partly derived from trivalent phosphorus, particularly in the case of PCl$_3$, the H$_3$PO$_3$ can be used in substoichiometric quantities. In that case, quantities of, for example, from 1 to 2 moles of H$_3$PO$_3$ per mole of chlorambucil are suitable. The hydrolysis products of PCl$_3$ which are formed during the reaction supply the quantities of the reactant additionally required for the reaction with trivalent phosphorus.

The reaction process can be carried out in the presence of, or, in special cases, even in the absence of inert solvents. The new process is prefeably carried out in the presence of inert solvents which are liquid at the reaction temperature.

In one preferred embodiment, the substituted butyric acid starting material is dissolved or suspended in an inert solvent, for example a halogenated hydrocarbon, such as chlorobenzene, and a mineral acid, particularly gaseous HCl, is added to the resulting solution or suspension before the reaction with H$_3$PO$_3$ and the dehydrating agent. The HCl is preferably used in a quantity at least stoichiometrically sufficient for salt formuation on the nitrogen mustard group, in which case it can be of advantage to carry out the reaction in a medium saturated with HCl gas. It has been found that the yield of the compound of formula II can be increased in this way. In one particularly suitable embodiment of the process of the invention, chlorambucil is initially introduced in solution in an inert solvent, the solution is saturated with HCl gas, $H_3PO_3$ is added in a molar ratio of about 1 to 2 moles of $H_3PO_3$ per mole of chlorambucil and, finally, $PCl_3$ is gradually added, preferably with stirring.

Saturation of the reaction medium with gaseous HCl is preferably carried out at temperatures of up to at most 40° C. Reaction of the starting material with phosphorous acid is then carried out at temperatures of, preferably, from about 60° to about 110° C. and more preferably at temperatures in the range of from about 70° to about 100° C.

The reaction product principally accumulating from the reaction of the chlorambucil with $H_3PO_3$ and the dehydrating phosphorus-halogen compound is hydrolyzed by the addition of water. The crude product of formula II which accumulates can be precipitated and purified by the addition of water-miscible solvents, for example acetone, optionally in conjunction with water. Pure compound of formula II normally accumulates in the form of a white powder which may optionally be converted into its acid addition salts or base addition salts in known manner.

The process information for the new compound of formula II, i.e., provided herein with reference to the special example of the reaction of chlorambucil, apply quite generally to other compounds of formula I. Accordingly, the present invention relates to a process for producing these new 1-hydroxy-1,1-diphosphonic acid compounds corresponding to general formula I and/or their salts, wherein the carboxyl group in the 1-position of substituted carboxylic acids corresponding to the following general formula

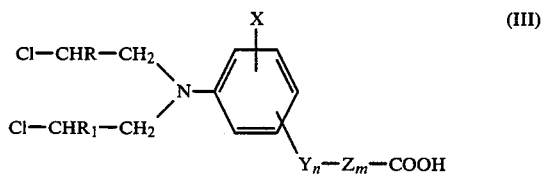

(III)

in which R, $R_1$, X, Y, Z, m and n are as defined above for compounds of formula I is converted into the 1-hydroxy-1,1-diphosphonic acid residue by reaction with $H_3PO_3$ and a dehydrating compound, particularly a phosphorus-halogen compound or anhydrous phosphoric acid, and the free acid is then optionally converted into its acid addition or base addition salt. In addition, the preferred process techniques described above with reference to the conversion of chlorambucil apply equally to the production of all of the new class of compounds of general formula I.

Compounds of formula III are known compounds or can readily be prepared using known methods. In particular, they can be prepared by the reaction of acetanilide or a substituted acetanilide with an anhydride or acid chloride monoester of a dicarboxylic acid in the presence of aluminum trichloride as a catalyst to obtain an ω-(4-acetaminophenyl)-oxo-carboxylic acid. The latter compound is reduced by known methods in an aqueous solution of sodium hydroxide to a 4-aminophenylcarboxylic acid, which is then reacted with an alkylene oxide, followed by treatment with phosphorus oxychloride to form a compound of formula III.

The pharmacological preparations of the invention which show cytostatic activity and, in particular, increased affinity for bone tumors and are useful in the treatment thereof contain the compounds of general formula I or their acid or base addition salts and, in particular, the compound of formula II and its salts in formulations normally used for oral, subcutaneous, intramuscular or intravenous treatment. The compounds of the invention may be formulated for administration in the form of tablets, pills, capsules or injection solutions. In addition to the pharmacologically active substance, standard pharmaceutical excipients can be present in liquid and/or solid form. The combined action mechanism of the new compounds are demonstrated on the one hand by scintigraphic measurements for tumor accumulation and, on the other hand, by testing cytostatic activity, particularly by determining tumor volume and/or the survival time of test animals.

Also, the compounds of formula I can be used in combination with known cytostatic agents, or in combination with other techniques useful in the treatment of bone tumors.

In addition, the compounds of the invention are useful in the treatment of gram-positive bacterial infections, in topical dosage forms such as in salve or lotion formulations, or for systemic use in the dosage forms described below.

The compounds of formula I can be formulated in finished unit dosage forms, e.g. capsules, tablets, sterile solutions for injection such as sterile isotonic solutions, etc., using known pharmaceutical adjuvant materials. Pharmaceutical adjuvant materials for oral dosage forms include, for example, inert diluents, such as calcium carbonate, sodium carbonate, lactose, calcium phosphate or sodium phosphate; granulating and disintegrating agents, for example, maize starch or alginic acid; binding agents, for example starch, gelatin or acacia; and lubricating agents, for example, magnesium stearate, stearic acid or talc.

The finished unit dosage form is formulated to contain from about 1 to about 200 mg. of a compound of formula I. The actual quantity of active compound chosen within the above range is dependent on the condition to be treated and the dosage frequency desired.

Mammalian patients to be treated with a compound of formula I are administered a cytostatic (cell growth inhititing) or antibacterial quantity of the compound of formula I, either continuously, e.g. by intravenous drip at a rate sufficient to produce a cytostatic or antibacterial effect, or intermittently at convenient intervals using a unit dosage form thereof.

The compounds of formula I can also be used to chelate calcium ions in water or in aqueous solutions containing such ions, in the same manner as other phosphonic acid derivatives having calcium ion chelating ability. Additionally, the compounds of formula I are useful as cross linking agents for cross linking polymers that contain amino groups, using standard reaction conditions well known to those skilled in the polymer art.

The invention will be better understood from the following examples, which are given for illustration purposes only and are not meant to limit the invention.

EXAMPLE 1

0.033 Mole of chlorambucil were dissolved in 75 ml of chlorobenzene in the absence of moisture in an inert gas atmosphere, after which hydrogen chloride was introduced for 30 minutes, resulting in the precipitation of a white deposit. The temperature was kept below 40° C. 0.05 Mole of phosphorous acid was then added, the mixture heated to 75° C. and 0.05 mole of phosphorus trichloride slowly added dropwise. After the dropwise addition, the mixture was heated for 30 minutes at 75°–80° C. and then for another 4 hours at 100° C.

The cooled reaction product was then hydrolyzed with 50 ml of water, resulting in the formation of a light brown paste from which the chlorobenzene phase was separated off. The light brown paste was triturated with acetone to form a white powder. A colorless crystalline product (the compound of formula II above) was filtered off and dried over phosphorus pentoxide.

Yield: 50%

Analysis: C 37.1, H 5.40, P 13.4, N 2.83, Cl 15.9, (37.33), (5.11), (13.78), (3.11), (15.78).

EXAMPLE 2

The acute toxicity of the compound of formula II (intravenous dose in the form of the disodium salt) was determined in mice (oral) with the following result: $DL_{50} > 625$ mg/kg, and in SD rats (i.v.) with the following results: $DL_{10}$-82 mg/kg, $DL_{50}$-146 mg/kg, $Dl_{50}$-0.32 mmole/kg When test animals (SD rates) implanted with osteosarcoma were given the compound of formula II paravenously or intravenously, a distinct accumulation of the new active substance in the bones and in the tumor was found by scintigraphic examination 16 hours after paravenous administration and 16 and 24 hours after intravenous administration.

In the determination of median survivaltimes (10 test animals per test and control group), an increase in the median survival time for the treated group of 128% over the untreated control group was observed after the administation of $10 \times 36.5$ mg/kg of the compound of formula II.

The development of the tumor volumes in relation to the untreated control group was significantly retarded both after the administration of $10 \times 36.5$ mg/kg of the compound of formula II and after the administration of $2 \times 73$ mg/kg of the compound of formula II.

What is claimed is:

1. A 1-hydroxy-1,1-diphosphonic acid compound of the formula

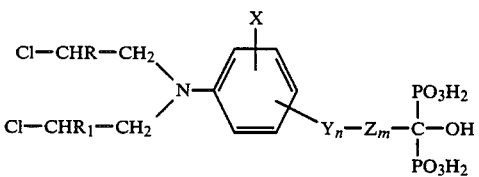

wherein R and $R_1$ can be the same or different and are hydrogen or methyl, x is hydrogen, halogen, an amino group optionally substituted with a lower acyl group, a lower alkyl group optionally substituted with an amino group or a lower acyl substituted amino group, or a lower alkoxy group, Y is O, S or NH, Z is a straight or branched chain $C_1$-$C_{10}$ alkylene group optionally substituted with an amino group or a lower acyl substituted amino group, m and n are the integers 0 or 1 with the proviso that when n is 1, m is also 1; and pharmaceutically acceptable acid or base addition salts thereof.

2. A 1-hydroxy-1,1-diphosphonic acid compound of claim 1 wherein R, $R_1$ and x are hydrogen, Z is a straight or branched chain $C_1$-$C_5$ alkylene radical, m is 0 or 1, and n is 0, and pharmaceutically acceptable acid or base addition salts thereof.

3. The compound of claim 1 which is 4-(4(bis-(2-chloroethyl)-amino)-phenyl)-1-hydroxy-butane-1,1-diphosphonic acid, or a pharmaceutically acceptable acid or base addition salt thereof.

4. A pharmaceutical composition in finished dosage form comprising:

(A) from about 1 to about 200 mg of a 1-hydroxy-1,1-diphosphonic acid compound of the formula

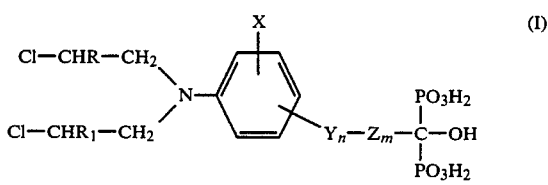

wherein R and $R_1$ can be the same or different and are hydrogen or methyl, x is hydrogen, halogen, an amino group optionally substituted with a lower acyl group, a lower alkyl group optionally substituted with an amino group or a lower acyl substituted amino group, or a lower alkoxy group, Y is O, S or NH, Z is a straight or branched chain $C_1$-$C_{10}$ alkylene group optionally substituted with an amino group or a lower acyl substituted amino group, m and n are the integers 0 or 1 with the proviso that when n is 1, m is also 1, or a pharmaceutically acceptable acid or base addition salt thereof; and (B) pharmaceutical adjuvant material.

5. A pharmaceutical composition in accordance with claim 4 wherein in the compound of formula I R, $R_1$, and X are hydrogen, Z is a straight or branched chain $C_1$-$C_5$ alkylene radical, m is 0 or 1, and n is 0.

6. A pharmaceutical composition in accordance with claim 4 wherein the compound of formula I is 4-(4-(bis-(2-chloroethyl)-amino)-phenyl)-1-hydroxy-butane-1,1-diphosphonic acid, or a pharmaceutically acceptable acid or base addition salt thereof.

7. A method of inhibiting cell growth in a mammal comprising treating said mammal with a cell growth-inhibiting quantity of a 1-hydroxy-1,1-diphosphonic acid compound of the formula

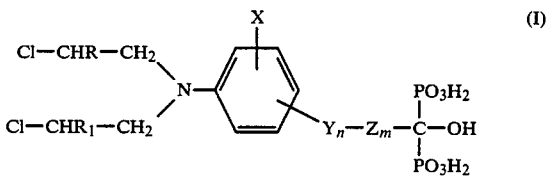

wherein R and $R_1$ can be the same or different and are hydrogen or methyl, x is hydrogen, halogen, an amino group optionally substituted with a lower acyl group, a lower alkyl group optionally substituted with an amino group or a lower acyl substituted amino group, or a lower alkoxy group, Y is O, S or NH, Z is a straight or branched chain $C_1$-$C_{10}$ alkylene group optionally substituted with an amino group or a lower acyl substituted amino group, m and n are the integers 0 or 1 with the proviso that when n is 1, m is also 1; or a pharmaceutically acceptable acid or base addition salt thereof.

8. A method in accordance with claim 7 wherein in the compound of formula I R, $R_1$, and X are hydrogen, Z is a straight or branched chain $C_1$–$C_5$ alkylene radical, m is 0 or 1, and n is 0, and pharmaceutically acceptable acid or base addition salts therof.

9. A method in accordance with claim 7 wherein the compound of formula I is 4-(4-(bis-(2-chloroethyl)-amino)-phenyl)-1-hydroxy-butane-1,1-diphosphonic acid, or a pharmaceutically acceptable acid or base addition salt thereof.

10. A method in accordance with claim 7 wherein the cell growth in the mammal are cells from a bone cancer.

11. A method in accordance with claim 10 where the bone cancer is osteosarcoma.

* * * * *